United States Patent [19]

Haensel

[11] Patent Number: 4,524,230

[45] Date of Patent: Jun. 18, 1985

[54] PREPARATION OF ALKYLAROMATIC COMPOUNDS

[75] Inventor: Vladimir Haensel, Hinsdale, Ill.

[73] Assignee: UOP Inc., Des Plaines, Ill.

[21] Appl. No.: 618,852

[22] Filed: Jun. 8, 1984

[51] Int. Cl.³ .............................................. C07C 3/52
[52] U.S. Cl. .................................... 585/467; 585/419;
585/446; 585/448; 208/112; 208/137; 208/138
[58] Field of Search ............... 585/446, 448, 467, 419;
208/81, 95, 112, 137, 138

[56] References Cited

U.S. PATENT DOCUMENTS

| | | | |
|---|---|---|---|
| 2,987,560 | 6/1961 | Holmes et al. | 585/419 |
| 3,109,038 | 10/1963 | Myers | 585/467 |
| 3,748,258 | 7/1973 | Cassidy et al. | 585/419 |
| 4,085,157 | 4/1978 | Juguin et al. | 585/419 |
| 4,193,895 | 3/1980 | Light et al. | 585/419 |
| 4,435,283 | 3/1984 | Buss et al. | 585/419 |
| 4,447,316 | 5/1984 | Buss | 585/419 |

FOREIGN PATENT DOCUMENTS 2360540  9/1975  France ................................ 585/419

Primary Examiner—D. E. Gantz
Assistant Examiner—A. Pal
Attorney, Agent, or Firm—William H. Page, II; Raymond H. Nelson

[57] ABSTRACT

Alkylaromatic compounds may be prepared by utilizing paraffinic hydrocarbon as an alkylating agent for the aromatic compound. The alkylation is effected in a fragmented scavenging reaction in which the paraffinic hydrocarbon acts as a fragment donor while the aromatic compound acts as a scavenging agent. The reaction is effected by decomposing a paraffinic hydrocarbon on the surface of a nonacid-acting catalyst at a temperature in the range of from about 50° to about 400° C. and a pressure in the range of from about 0.33 atmospheres to about 50 atmospheres.

14 Claims, No Drawings

PREPARATION OF ALKYLAROMATIC COMPOUNDS

BACKGROUND OF THE INVENTION

Alkylaromatic compounds will find a wide variety of uses in the chemical field. For example, toluene is used as a blending stock for aviation gasoline and a high octane gasoline, as a solvent, as an intermediate in medicines, dyes, perfumes, explosives, etc. Ethylbenzene is used in flavoring extracts, perfumes, in solvent mixtures, lacquers, as a solvent for cellulose derivatives as well as natural and synthetic resins and as an intermediate for the preparation of styrene. In like manner, n-butylbenzene is used in organic synthesis while relatively long chain alkylbenzenes such as dodecylbenzene, tridecylbenzene, tetradecylbenzene, pentadecylbenzene, if in essentially linear form and with a minimum amount of branching being present, are used as detergent alkylates which may be sulfonated and neutralized. The linear detergent alkylates are especially preferred due to the biodegradability of the molecule when used in detergents, thus eliminating the unwanted presence or build-up of unsightly and potentially hazardous foams in water which may be a source for drinking, cooking, etc.

The alkylation of aromatic compounds utilizing olefins or haloalkyl radicals as alkylating agents is known in the art. The alkylation with these alkylating agents is effected in the presence of catalysts of the Friedel Crafts type such as aluminum chloride, zirconium chloride, iron chloride, etc., or using other acid-acting catalysts such as boron trifluoride, sulfuric acid, etc.

As will hereinafter be shown in greater detail, it has now been discovered that aromatic compounds may be alkylated utilizing a relatively inexpensive paraffinic hydrocarbon of the type hereinafter set forth in greater detail as an alkylating agent.

BRIEF SUMMARY OF THE INVENTION

This invention relates to a process for the preparation of an alkylaromatic compound. More particularly, the invention is concerned with a process for the alkylation of an aromatic compound utilizing a paraffinic hydrocarbon as an alkylating agent. As was previously mentioned, alkylaromatic compounds can be prepared by reacting an aromatic compound in the presence of certain catalytic compositions of matter while employing a relatively inexpensive alkylating agent, namely, paraffinic hydrocarbon. Paraffinic hydrocarbons are more prevalent in the petrochemical industry and therefore are relatively more inexpensive than olefins. Such paraffins may have to be subjected to a dehydrogenation reaction to obtain the necessary compound or haloalkyl compounds which must be subjected to a halogenation reaction in order to render the same available for use as the desired alkylating agent. By utilizing paraffinic hydrocarbons, and preferably those which are linear in nature, for certain reactions, it is possible to obtain a linear alkylaromatic compound which, as hereinbefore set forth, in the case of detergent alkylates constitutes a preferred reaction product. Likewise, when the paraffinic hydrocarbon contains some branching, it is possible, by utilizing the process of the present invention, to obtain an alkylaromatic product in which the branching of the chain is in substantially the same position in the product as it was in the alkylating agent.

It is therefore an object of this invention to provide a process for preparing an alkylaromatic compound. A further object of this invention is to provide a process for preparing an alkylaromatic compound utilizing inexpensive alkylating agents in reaction with an aromatic compound to produce the desired product.

In one aspect an embodiment of this invention will be found in a process for the preparation of an alkylaromatic compound which comprises decomposing a paraffinic hydrocarbon on the surface of a nonacid-acting catalyst containing a metal of Group VIII of the Periodic Table at decomposition conditions, scavenging the fragments of said paraffinic hydrocarbon from the surface of said catalyst with a scavenging agent comprising an aromatic compound, and recovering the resultant alkylaromatic compound.

A specific embodiment of this invention is found in a process for the preparation of ethylbenzene which comprises decomposing propane on the surface of a nonacid-acting catalyst comprising nickel composited on kieselguhr at a temperature in the range of from about 50° to about 400° C. and a pressure in the range of from subatmospheric to about 50 atmospheres, scavenging the fragments of said propane from the surface of said catalyst with benzene, and recovering the resultant ethylbenzene.

Other objects and embodiments will be found in the following further detailed description of the invention.

DETAILED DESCRIPTION OF THE INVENTION

As hereinbefore set forth, the present invention is concerned with a process for the preparation of alkylaromatic compounds utilizing as the alkylating agent therefor a paraffinic hydrocarbon. The alkylation of the aromatic compound is effected in a fragment scavenging reaction in which the paraffinic hydrocarbon acts as a fragment donor while the aromatic compound acts as a scavenging agent. The alkylation reaction is effected by decomposing a paraffinic hydrocarbon on the surface of a nonacid-acting catalyst at decomposition conditions and scavenging the fragments of the decomposed paraffinic hydrocarbon from the surface of the catalyst with an aromatic compound of the type hereinafter set forth in greater detail. The reaction or decomposition conditions which are employed to effect the desired reaction will include elevated temperatures in the range of from about 50° to about 400° C., and pressures which will range from subatmospheric, that is, from about 0.33 atmospheres, up to about 50 atmospheres or more. The superatmospheric pressures may be afforded by the autogeneous pressure of the paraffinic hydrocarbon, if in gaseous form, or by the introduction of a substantially inert gas such as nitrogen, helium, argon, etc., into the reaction vessel.

As was previously set forth, the alkylating agent in the process of the present invention comprises a paraffinic hydrocarbon, the term "paraffinic hydrocarbon" as used in the present specification and appended claims, will include linear straight chain paraffins or branched chain paraffins containing from 2 to about 16 carbon atoms or cycloparaffinic hydrocarbons containing from 3 to about 8 carbon atoms. Some specific examples of these paraffinic hydrocarbons will include linear paraffins such as ethane, propane, n-butane, n-pentane, n-hexane, n-heptane, n-octane, n-nonane, n-decane, n-undecane, n-dodecane, n-tridecane, n-tetradecane, n-pentadecane, n-hexadecane, etc; branched chain paraffins such as isobutane, isopentane, isohexane, 2,2-dimethylbutane, 2,3-dimethylpentane, 2,3-dimethylhexane, 2,4-dimethylheptane, 2-methyloctane, 2,3-dimethyloctane, 2,4-dimethylnonane, 2-methylnonane, 2,3-dimethylnonane, 3,4-dimethyldecane, 2,2-dimethyldecane, 2,4-dimethylundecane, etc; and cycloparaffins such as cyclopropane, cyclobutane, cyclopentane, cyclohexane, cycloheptane, cyclooctane, etc.

The scavenging agent which will scavenge the fragmented donor from the surface of the catalyst and thus form the desired alkylaromatic compound will include both mononuclear and polynuclear aromatics, said aromatics being substituted or unsubstituted in nature. In the event that the aromatic compounds are in substituted form, the substituents on the ring will be limited to those substituents which are not readily degraded during the reaction while utilizing the nonacidic catalyst. Some representative examples of aromatic compounds which are employed as the scavenging agents will include: benzene, toluene, ethylbenzene, o-xylene, m-xylene, p-xylene, n-propylbenzene, cumene, naphthalene, 1-methylnaphthalene, 2-methylnaphthalene, 1-ethylnaphthalene, 2-ethylnaphthalene, anthracene, 1-methylanthracene, 2-methylanthracene, biphenyl, etc. It is to be understood that the aforementioned alkylating agents which are fragment donors and aromatic compounds which are scavenging agents are only representative of the type of compounds which may be employed and that the present invention is not necessarily limited thereto.

The catalyst which is employed to effect the alkylation reaction of the present invention in which a donor hydrocarbon, either paraffinic or cycloparaffinic in nature, is deposited on the surface of said catalyst and the fragment of the donor compound acts as an alkylating agent for reaction with a scavenging compound such as an aromatic compound of the type hereinbefore set forth in greater detail, will comprise a nonacid-acting catalyst. The catalyst must possess the ability of being strong enough to induce a cleavage of the carbon-carbon bond, preferably at the alpha carbon atom as well as being able to activate the scavenging compound at relatively low temperatures within the range which has also been hereinbefore set forth. The ability of the catalyst to induce breakage of the carbon bond and to activate the scavenging agent will act to prevent a carbonization on the surface of the catalyst, thereby increasing the active life of said catalyst.

The alkylation catalyst which is employed will be a nonacidacting catalyst in which the active metallic component of the catalyst will be either unsupported or composited on a nonacid-acting support. In the preferred embodiment of the invention, the catalyst will comprise a metal of Group VIII of the Periodic Table, said metals being exemplified by nickel, iron, cobalt as well as the noble metals of Group VIII of the Periodic Table, such as platinum, palladium, rhodium, ruthenium, osmium and iridium. Of the aforementioned metals, a nonnoble metal such as nickel, iron and cobalt, constitute a possible preferred metallic component of the catalyst. It is also contemplated within the scope of this invention that mixtures of noble and non-noble metals such as nickel-platinum, nickel-palladium, iron-platinum, iron-palladium, cobalt-rhodium, cobalt-ruthenium, etc. may also be employed as alkylation catalysts, although not necessarily with equivalent results. As examples of nonacid-acting catalyst supports which may be utilized, kieselguhr, silica or acid-clays such as montmorillonite, bentonite or various zeolites such as aluminosilicates of varying compositions which are well known in the art, or alumina may be used, said clays, zeolites and alumina having been neutralized by treatment with an alkali material such as sodium hydroxide, potassium hydroxide, lithium hydroxide, etc. to eliminate the acidity of the support. In the preferred embodiment of the invention, the catalytic metal portion of the finished catalyst composition will be present therein in an amount in the range of from about 0.1% to about 70% by weight of the finished composition. Some representative examples of nonacid-acting catalysts which may be employed will include elemental nickel, Raney nickel, elemental cobalt, Raney cobalt, iron, nickel composited on kieselguhr, nickel composited on silica, nickel composited on neutralized zeolites, cobalt composited on kieselguhr, cobalt composited on silica, cobalt composited on neutralized zeolites, iron composited on kieselguhr, iron composited on silica, iron composited on neutralized zeolites, etc. It is to be understood that the aforementioned list of catalysts are only representative, being used to illustrate the type of catalyst which may be employed, and that the present invention is not necessarily limited thereto.

The alkylation process of the present invention may be effected in any suitable manner and may comprise either a batch or continuous type operation. For example, when a batch type operation is employed, a quantity of the catalyst is placed in a desired reaction apparatus. The apparatus which is employed will be dependent upon the particular operating conditions which are used to effect the reaction and will include such apparatus which may be used for vacuum operations when subatmospheric pressures are employed, vessels such as flasks when atmospheric pressures are employed or pressure-resistant vessels such as autoclaves of the rotating, stirring or mixing type when superatmospheric pressures are employed. The reaction vessel containing the catalytic composition of matter is brought to the desired operating temperature and pressure by external means and the alkylating agent comprising the paraffinic or cycloparaffinic compound is passed over the catalyst to effect a decomposition thereof. Following the introduction of the donor compound for a predetermined period of time and operating conditions, the donee or scavenging compound comprising the aromatic compound is then introduced into the reaction vessel and passed over the catalyst to effect the desired alkylation reaction in which the fragmented donor compound reacts with the donee compound to form the desired alkylaromatic compound. Alternatively, a simultaneous introduction of the paraffinic donor compound and the aromatic donee compound into the reactor for contact with the catalyst may be employed to effect the reaction. The reaction mixture, after expiration of the predetermined residence time which may range from about 0.5 seconds up to about 0.5 hour or more in duration, is recovered and subjected to conventional means of separation such as fractional distillation under reduced pressure whereby the desired alkylaromatic is separated from any unreacted aromatic compound, alkylating agent or side reaction products, and recovered.

It is also contemplated within the scope of this invention that the alkylation process involving the decomposition of the donor compound such as a paraffinic compound with the attendant scavenging of the fragments by an aromatic compound to form the desired alkylaromatic compound may be effected in a continuous manner of operation. When such a type of operation is employed, the nonacidacting catalyst of the type hereinbefore more fully described is placed in an appropriate reactor and is maintained at the proper operating conditions of temperature and pressure. The donor compound comprising a paraffinic compound and the donee compound comprising an aromatic compound, respectively, are continuously charged to this reactor at a predetermined space velocity. The reactants are contacted with the catalyst whereby the paraffinic hydrocarbon is decomposed into fragments which are swept up by the scavenging compound comprising the aromatic compound to form the alkylaromatic compound, and after passage through the reactor, also for a predetermined period of time, the reactor effluent is continuously withdrawn and subjected to conventional means of separation such as distillation, whereby the desired alkylaromatic compound is separated and recovered while any unreacted starting materials are recycled back to the reactor zone. The mole ratios of donor compound to donee compound may vary over a previously determined range, depending upon the amount of alkylation desired, that is, whether mono- or polyalkylation of the aromatic compound is the desired goal. Generally speaking, the paraffinic compound may be present in the feedstream in an amount in the range of from about 0.1:1 to about 20:1 moles of paraffinic compound per mole of aromatic compound.

Inasmuch as the alkylation catalyst which is nonacidacting in character is in solid form, various types of continuous operations may be employed. In one type of operation, the catalyst may be situated in the reactor as a fixed bed and the reactants passed over the catalyst bed in either an upward or downward flow. Another type of operation which may be employed constitutes the moving bed type of operation in which the catalyst bed and the reactant are passed through the reactor either concurrently or countercurrently to each other. A third type of continuous operation which may be used comprises the slurry type in which the catalyst is passed into the reactor as a slurry in the feedstream. Regardless of which type of operation is employed, the reactor effluent is continuously withdrawn and treated in a manner similar to that hereinbefore set forth.

Under some circumstances, a portion of the fragments resulting from the decomposition of the donor compound may undergo a polymerization reaction to deposit the thus formed polymerization products on the surface of the catalyst, this deposition resulting in a decrease in the activity of the catalyst. It is contemplated within the scope of the invention that the regeneration of the catalyst may be accomplished by the periodic introduction of specified amounts of hydrogen into the reaction zone whereby the aforesaid polymerization products may be removed from the surface of the catalyst, thereby restoring the activity of the catalyst to the desired levels.

Some specific examples of alkylaromatic compounds which may be obtained by utilizing the process of this invention will include toluene, ethylbenzene, n-propylbenzene, n-butylbenzene, n-pentylbenzene, neopentylbenzene, n-hexylbenzene, n-heptylbenzene, n-decylbenzene, n-undecylbenzene, n-dodecylbenzene, n-tridecylbenzene, n-tetradecylbenzene, n-pentyldecylbenzene, o-xylene, m-xylene, p-xylene, o-ethyltoluene, m-ethyltoluene, p-ethyltoluene, o-diethylbenzene, m-diethylbenzene, p-diethylbenzene, o-di-n-propylbenzene, m-di-n-propylbenzene, p-di-n-propylbenzene, 1-methylnaphthalene, 1-ethylnaphthalene, 1-n-propylnaphthalene, 1-methyl-2-ethylnaphthalene, 1-methyl-4-ethylnaphthalene, 1-methyl-2-n-propylnaphthalene, 1-methyl-4-n-propylnaphthalene, 1-methylanthracene, 2-methylanthracene, 1,4-dimethylanthracene, 1,4-diethylanthracene, etc. It is to be understood that these compounds are merely representative of the class of alkylaromatic compounds which may be obtained when utilizing the herein described process, and that the present invention is not necessarily limited thereto.

The following examples are given for purposes of illustrating the present process. However, it is to be understood that they are merely illustrative in nature and that the present invention is not necessarily limited thereto.

EXAMPLE I

A catalyst comprising 66% nickel deposited on kieselguhr in the form of ⅛″ cylindrical pellets was placed in a glass reactor which was inserted into a furnace. The reactor was heated to an initial temperature of 100° C. and raised during the reaction period from this temperature to 250° C. Propane gas was bubbled through benzene at room temperature and the vaporous mixture of propane and benzene was passed into the reactor over the catalyst. The reaction was continuously monitored during this period by means of mass spectroscopy. It was observed that when the temperature reached 195° C., the concentration of methane from the fragmented propane declined while the ethane concentration remained high. The formation of toluene and ethylbenzene was also observed by mass spectroscopy, the latter being separated and recovered.

When the above experiment was repeated using a pulse feed operation in which pulses of propane and pulses of benzene were introduced into the reactor at a gaseous hourly space velocity of propane of 1000 and a liquid hourly space velocity of benzene of 0.9 in alternate pulses, ethylbenzene was also formed.

EXAMPLE II

In this example, a catalyst comprising nickel composited on kieselguhr in an amount so that nickel may be present in 58% by weight of the catalyst, may be placed in a reaction flask. The flask may be heated to a temperature of 245° C. while maintaining atmospheric pressure and simultaneously streams of benzene and n-tetradecane may be passed over the catalyst. The resulting reaction product which may contain unconverted benzene and n-tetradecane as well as toluene and n-tridecylbenzene may be recovered and the latter product, namely, n-tridecylbenzene, may be separated from the other components of the mixture.

EXAMPLE III

A catalyst comprising 0.5% by weight of platinum composited on silica may be placed in a vacuum apparatus which may be maintained at a subatmospheric pressure of 0.5 atmospheres. A donor compound comprising n-butane and a donee compound comprising biphenyl may be simultaneously charged to the reactor and after passage through the reactor for a period of 1.5 minutes, the reaction product comprising a mixture of unconverted biphenyl, n-butane, toluene, and n-propylbenzene may be recovered and subjected to distillation whereby the n-propylbenzene may be separated and recovered.

EXAMPLE IV

A catalyst comprising 30% cobalt composited on kieselguhr may be placed in a rotating autoclave which is sealed. A feed stream comprising propane as a donor compound may be charged to the reactor which is heated to a temperature of 225° C., the amount of propane charged being sufficient to attain a pressure of 5 atmospheres. The donee compound comprising ethylbenzene may then be charged to the autoclave and the reaction allowed to proceed for a period of 10 minutes. At the end of this time, heating may be discontinued and after the autoclave and contents thereof have returned to room temperature, any excess pressure which may still be present is vented. The reaction product comprising a mixture of unreacted ethylbenzene along with a mixture of diethylbenzene may be recovered and the desired product comprising the aforementioned mixture of diethylbenzene may be separated from the unreacted ethylbenzene.

EXAMPLE V

A catalyst comprising iron composited on kieselguhr may be placed in a reaction vessel which may be heated to a temperature of 300° C. The reaction components comprising propane and p-xylene in an amount sufficient to maintain a propane to p-xylene ratio of 1:1 may be passed over the catalyst at a liquid hourly space velocity based on the p-xylene of 1. The reaction product mixture which may comprise unconverted p-xylene, propane, along with p-ethyltoluene, may be recovered from the reactor and separated by conventional means to permit recovery of the desired product comprising p-ethyltoluene.

EXAMPLE VI

In this example, a catalyst comprising nickel composited on kieselguhr may be placed in a reaction vessel which may then be heated to a temperature of about 200° C. The donor compound comprising 2-2-dimethylbutane (neohexane) along with the donee compound comprising benzene may be added to the reaction vessel which is maintained at the aforementioned temperature and an atmospheric pressure. Upon completion of the desired residence time for the reaction, the reaction product comprising unconverted benzene, neohexane, toluene and neopentylbenzene may be recovered from the reactor and the desired product comprising neopentylbenzene may be separated from other components of the mixture by conventional means.

I claim as my invention:

1. A process for the alkylation of an aromatic scavenger compound with a paraffinic hydrocarbon to produce a resultant alkylaromatic compound by means of attachment of a fragment of said paraffinic hydrocarbon to said aromatic compound which comprises decomposing said paraffinic hydrocarbon on the surface of a nonacid-acting catalyst containing at least one metal of Group VIII of the Periodic Table at a temperature of about 50° to about 400° C. and a pressure in the range of from about subatmospheric to about 50 atmospheres to produce fragments of said paraffinic hydrocarbon and contacting said nonacid-acting catalyst having said fragment of said decomposed paraffin thereon with said aromatic scavenger compound as a scavenging agent to scavenge said fragments of said paraffinic hydrocarbon to attach said fragment of said paraffinic hydrocarbon to said aromatic compound to form said alkylaromatic compound, and recovering said alkylaromatic compound.

2. The process as set forth in claim 1 in which said paraffinic hydrocarbon is selected from the group consisting of linear paraffins, branched chain paraffins and cycloparaffins.

3. The process as set forth in claim 1 in which said aromatic compound is selected from the group consisting of unsubstituted and substituted mononuclear and polynuclear aromatic compounds.

4. The process as set forth in claim 1 further characterized in that said metal of Group VIII of the Periodic Table comprising the catalyst is composited on a nonacidic solid support.

5. The process as set forth in claim 4 in which said catalyst comprises nickel composited on kieselguhr.

6. The process as set forth in claim 4 in which the catalyst comprises cobalt composited on kieselguhr.

7. The process as set forth in claim 4 in which the catalyst comprises platinum composited on silica.

8. The process as set forth in claim 4 in which the catalyst comprises nickel composited on a neutralized aluminosilicate.

9. The process as set forth in claim 4 in which the catalyst comprises iron composited on kieselguhr.

10. The process as set forth in claim 1 in which said paraffinic hydrocarbon is propane, said scavenger aromatic compound is benzene and said alkylaromatic compound is ethylbenzene.

11. The process as set forth in claim 1 in which said paraffinic hydrocarbon is n-tetradecane, said scavenger aromatic compound is benzene and said alkylaromatic compound is n-tridecylbenzene.

12. The process as set forth in claim 1 in which said paraffinic hydrocarbon is propane, said scavenger aromatic compound is ethylbenzene and said alkylaromatic compound is diethylbenzene.

13. The process as set forth in claim 1 in which said paraffinic hydrocarbon is propane, said scavenger aromatic compound is p-xylene and said alkylaromatic compound is p-ethyltoluene.

14. The process as set forth in claim 1 in which said paraffinic hydrocarbon is butane, said scavenger aromatic compound is biphenyl and said alkylaromatic compound is n-propylbenzene.

* * * * *